US008362559B2

(12) United States Patent
Tour et al.

(10) Patent No.: US 8,362,559 B2
(45) Date of Patent: Jan. 29, 2013

(54) HYBRID MOLECULAR ELECTRONIC DEVICES CONTAINING MOLECULE-FUNCTIONALIZED SURFACES FOR SWITCHING, MEMORY, AND SENSOR APPLICATIONS AND METHODS FOR FABRICATING SAME

(75) Inventors: James M. Tour, Bellaire, TX (US); Michael P. Stewart, Mountain View, CA (US); Jianli He, Houston, TX (US); Harry F. Pang, Houston, TX (US)

(73) Assignee: William Marsh Rice University, Houston, TX (US)

( * ) Notice: Subject to any disclaimer, the term of this patent is extended or adjusted under 35 U.S.C. 154(b) by 446 days.

(21) Appl. No.: 12/754,268

(22) Filed: Apr. 5, 2010

(65) Prior Publication Data

US 2010/0252824 A1    Oct. 7, 2010

Related U.S. Application Data

(63) Continuation-in-part of application No. 12/407,471, filed on Mar. 19, 2009, now Pat. No. 7,838,077, which is a continuation of application No. 11/619,073, filed on Jan. 2, 2007, now Pat. No. 7,527,831, which is a continuation of application No.

(Continued)

(51) Int. Cl.
*H01L 27/01* (2006.01)
*H01L 27/12* (2006.01)
*H01L 35/24* (2006.01)
*H01L 51/00* (2006.01)
*H01L 23/58* (2006.01)

(52) U.S. Cl. ............ 257/347; 257/40; 257/642; 257/57

(58) Field of Classification Search .................. 257/347, 257/40, 765, 253, 288, 414, 213, 365, 310, 257/316, 508, 633, 22, 642, 643, 57, 59, 257/348, 349
See application file for complete search history.

(56) References Cited

U.S. PATENT DOCUMENTS

| | | |
|---|---|---|
| 4,514,263 A | 4/1985 | Janata et al. |
| 5,429,708 A | 7/1995 | Linford et al. |
| 5,554,739 A | 9/1996 | Belmont |
| 5,719,033 A | 2/1998 | Ackley et al. |
| 5,869,550 A | 2/1999 | Mahmud et al. |

(Continued)

FOREIGN PATENT DOCUMENTS

| | | |
|---|---|---|
| WO | 02/060812 | 8/2002 |
| WO | 03/032330 | 4/2003 |

OTHER PUBLICATIONS

Cahen, et al., "Molecules and Electronic Materials", Adv. Mater., 14:2002, pp. 789-798.

(Continued)

*Primary Examiner* — Chuong A. Luu
(74) *Attorney, Agent, or Firm* — Winstead PC

(57) ABSTRACT

This invention is generally related to a method of making a molecule-surface interface comprising at least one surface comprising at least one material and at least one organic group wherein the organic group is adjoined to the surface and the method comprises contacting at least one organic group precursor with at least one surface wherein the organic group precursor is capable of reacting with the surface in a manner sufficient to adjoin the organic group and the surface. The present invention is directed to hybrid molecular electronic devices having a molecule-surface interface. Such hybrid molecular electronic devices may advantageously have either a top or bottom gate electrode for modifying a conductivity of the devices.

22 Claims, 8 Drawing Sheets

Related U.S. Application Data

10/356,841, filed on Feb. 3, 2003, now Pat. No. 7,176,146, application No. 12/754,268, which is a continuation-in-part of application No. 11/157,391, filed on Jun. 21, 2005, now abandoned.

(60) Provisional application No. 60/353,120, filed on Feb. 1, 2002, provisional application No. 60/581,492, filed on Jun. 21, 2004, provisional application No. 60/581,409, filed on Jun. 21, 2004.

(56) References Cited

U.S. PATENT DOCUMENTS

| | | | |
|---|---|---|---|
| 6,042,643 | A | 3/2000 | Belmont et al. |
| 6,217,740 | B1 | 4/2001 | Andrieux et al. |
| 6,284,317 | B1 | 9/2001 | Laibinis et al. |
| 6,368,239 | B1 | 4/2002 | Devonport et al. |
| 6,430,511 | B1 | 8/2002 | Tour et al. |
| 6,433,356 | B1 | 8/2002 | Cahen et al. |
| 6,724,009 | B2 | 4/2004 | Cerofolini et al. |
| 6,827,979 | B2 | 12/2004 | Mirkin et al. |
| 6,890,806 | B2 | 5/2005 | Cerofolini et al. |
| 6,986,943 | B1 | 1/2006 | Cook et al. |
| 7,019,343 | B2 | 3/2006 | Chou et al. |
| 7,061,011 | B2 * | 6/2006 | Forrest et al. ............... 257/40 |
| 7,112,366 | B2 | 9/2006 | McCreery et al. |
| 7,324,385 | B2 * | 1/2008 | Mobley et al. ........... 365/185.29 |
| 7,326,957 | B2 * | 2/2008 | Halik et al. .................. 257/40 |
| 7,358,113 | B2 * | 4/2008 | Shrivastava et al. ............ 438/99 |
| 8,193,304 | B2 * | 6/2012 | Yamamoto et al. ........... 528/377 |
| 2002/0109192 | A1 | 8/2002 | Hogyoku et al. |
| 2003/0058697 | A1 | 3/2003 | Tour et al. |
| 2004/0007740 | A1 | 1/2004 | Abstreiter et al. |
| 2004/0195563 | A1 | 10/2004 | Bao et al. |
| 2004/0200734 | A1 | 10/2004 | Co et al. |
| 2004/0238379 | A1 | 12/2004 | Lindsay et al. |
| 2005/0179065 | A1 | 8/2005 | Chou et al. |
| 2006/0051919 | A1 | 3/2006 | Mascolo et al. |
| 2006/0051946 | A1 | 3/2006 | Mascolo et al. |
| 2008/0236666 | A1 | 10/2008 | Bidan et al. |

OTHER PUBLICATIONS

Yaliraki, et al., "Interplay of Topology and Chemical Stability on the Electronic Transport of Molecular Junctions", Ann. N.Y. Acad. Sci., 960:2002, pp. 153-162.
Ulman, "Formation and Structure of Self-Assembled Monolayers", Chem. Rev., 96:1996, pp. 1533-1554.
Buriak, "Organometallic Chemistry on Silicon and Germanium Surfaces", Chem. Rev., 102:2002, pp. 1272-1308.
Seker, et al., "Surface Chemistry of Prototypical Bulk II-VI and III-V Semiconductors and Implications for Chemical Sensing", Chem. Rev., 100:2000, pp. 2505-2536.
Chen, et al., "Large On-Off Ratios and Negative Differential Resistance in a Molecular Electronic Device", 286:1999, pp. 1550-1552.
Tour, "Molecular Electronics. Synthesis and Testing of Components", Acc. Chem. Res., 33:2000, pp. 791-804.
Reed, et al., "Molecular random access memory cell", App. Phys. Lett., 78:2001, pp. 3735-3739.
Villeneuve, et al., "Electrochemical Formation of Close-Packed Phenyl Layers on Si(111)", J. Phys. Chem. B, 101: 1997, pp. 2415-2420.
Combellas, et al., "Surface modification of halogenated polymers. 4. Functionalisation of poly(tetrafluoroethylene) surfaces by diazonium salts", Polymer, 44:2003, pp. 19-24.
Wade, et al., "Preparation of Pit-Free Hydrogen-Terminated Si(111) in Deoxygenated Ammonium Fluoride", Mat. Res. Soc. Symp. Proc., 477:1997, pp. 299-304.
Higashi, et al., "Ideal hydrogen termination of the Si(111) surface", Appl. Phys. Lett., 56:1990, pp. 656-658.
Schmid, et al., "Current and Future Applications of Nanoclusters", Chem. Soc. Rev., 1999, pp. 179-185.
Parikh, et al., "Quantitative determination of molecular structure in multilayered thin films of biaxial and lower symmetry from photon spectroscopies. I. Reflection infrared vibrational spectroscopy", J. Chem. Phys., 96:1992, pp. 927-945.
Tour, et al., "Synthesis and Preliminary Testing of Molecular Wires and Devices", Chem. Eur. J., 7:2001, pp. 5118-5134.
Kosynkin, et al., "Phenylene Ethynylene Diazonium Salts as Potential Self-Assembling Molecular Devices", Org. Lett., 3:2001, pp. 993-995.
International Search Report and Written Opinion for PCT/US05/21861 mailed Mar. 27, 2007.
International Search Report for PCT/US03/03096 mailed Apr. 26, 2005.
Stewart, et al., "Direct Covalent Grafting of Conjugated Molecules onto Si, GaAs, and Pd Surfaces from Aryldiazonium Salts", J. Am. Chem. Soc., 126:2004, pp. 370-378.
Liu, et al., "Reactions of Organic Monolayers on Carbon Surfaces Observed with Unenhanced Raman Spectroscopy", J. Am. Chem. Soc., 117:1995, pp. 11254-11259.
Cheng, et al., "Molecular Electronics: NanoCell Electronic Memories and Direct Covalent Attachment of Molecules to Oxide-Free Silicon for Construction of Hybrid Devices", Science Technica, 2004, pp. 199-203.
Cerefolini, "Realistic limits to computation. II. The technological side", App. Phys. A, 86:2007, pp. 31-42.
He, et al., Controllable Molecular Modulation of Conductivity in Silicon-Based Devices, J. Am. Chem. Soc., 131:2009, pp. 10023-10030.
Lu, et al., "Direct Covalent Grafting of Polyoxometalates onto Si Surfaces", Chem. Mater., 21:2009, pp. 442-446.
He, et al., "Reversible Modulation of Conductance in Silicon Devices via UV/Visible-Light Irradiation", Adv. Mater., 20:2008, pp. 4541-4546.
Lu, et al., "Surface Grafting of Ferrocene-Containing Triazene Derivatives in Si(100)", Chem. Mater., 20:2008, pp. 7352-7355.
He, et al., "Silicon/Molecule Interfacial Electronic Modifications", J. Am. Chem. Soc., 130:2008, pp. 1699-1710.
Flatt, et al., "Attaching Electronically Active Oligoanilines to Silicon Surfaces", Chem. Mater., 18:2006, pp. 4513-4518.
Cerefolini, et al., "A hybrid approach to nanoelectronics", Nanotechnology, 16:2005, pp. 1040-1047.
Cerefolini, et al., "Strategies for nanoelectronics", Microelectronic Eng., 81:2005, pp. 405-419.
Cerefolini, et al., "Allowing electronics to face the TSI era—Molecular electronics and beyond", STMicroelectronics, Post-Silicon Technology, 20041 Milan, Italy Feb. 5, 2007, 50 pages.
Cerefolini, et al., "A hybrid micro-nano-molecular route for nonvolatile memories", Semicond. Sci. Tech., 21:2006, pp. 1315-1327.

* cited by examiner

HYBRID MOLECULAR ELECTRONIC DEVICES CONTAINING MOLECULE-FUNCTIONALIZED SURFACES FOR SWITCHING, MEMORY, AND SENSOR APPLICATIONS AND METHODS FOR FABRICATING SAME

CROSS-REFERENCE TO RELATED APPLICATIONS

This application is a continuation-in-part of U.S. patent application Ser. No. 12/407,471, filed Mar. 19, 2009 now U.S. Pat. No. 7,838,077, which is a continuation of U.S. patent application Ser. No. 11/619,073 (now U.S. Pat. No. 7,527,831), filed Jan. 2, 2007, which is a continuation of U.S. patent application Ser. No. 10/356,841 (now U.S. Pat. No. 7,176,146), filed Feb. 3, 2003, which claims the priority of U.S. Provisional Patent Application 60/353,120, filed Feb. 1, 2002. This application is also a continuation-in-part of U.S. patent application Ser. No. 11/157,391, filed Jun. 21, 2005, now abandoned which claims the priority of U.S. Provisional Patent Applications 60/581,409, filed Jun. 21, 2004 and 60/581,492, filed Jun. 21, 2004. Each of these prior applications are incorporated by reference in their entirety herein.

STATEMENT REGARDING FEDERALLY SPONSORED RESEARCH

This invention was made with Government support under Grant Nos. N00014-01-1-0657, N00014-04-1-0765 and N00014-99-1-0406, all awarded by the United States Department of Defense. The Government has certain rights in the invention.

FIELD OF THE INVENTION

This invention is generally related to a method of making a molecule-surface interface. The surface comprises at least one material and at least one organic group adjoined to the surface. The method comprises contacting at least one organic group precursor with at least one surface wherein the organic group precursor is capable of reacting with the surface in a manner sufficient to adjoin the organic group and the surface. The present invention also relates generally to the field of molecular electronics, and more particularly relates to a hybrid molecular electronic device incorporating solid-state and molecular components.

BACKGROUND OF THE INVENTION

Modern solid-state electronic devices, such as transistors and other circuits and switches, rely on high-quality, easily manufactured electrical interconnects, where an interconnect comprises a point of contact between at least two different materials. Key to the proper function of such interconnect devices is the robustness of the interconnect and its ability to reliably conduct electronic signals such as current and potential. Additionally, interconnect devices may also be required to conduct photons as for example to transmit light-based signals. Dependable techniques of manufacturing strive to consistently create high-quality, defect-free interconnects. Such devices fail when contact across the interconnect is impeded or prevented. For example, at small dimensions surface roughness at the contact boundary can make it difficult to achieve or maintain contact sufficient to ensure proper electrical conduction. At dimensions approaching the nanometer scale, normal surface topology of metal surfaces ordinarily used in interconnects can prevent large portions of the corresponding surfaces from establishing contact. These gaps substantially increase the electrical resistance in the interconnect device and often result in an interconnect device that cannot adequately conduct electrical current.

Recent advances in nanotechnology have made it possible to consider the smallest possible sizes for electronic devices. Namely, circuits and devices, including electrical interconnects, employing devices that comprise one or a small collection of molecules are now within the realm of plausible device structures. Engineering good contacts at the molecular level poses a significant challenge. As the fabrication of coherent molecular electronic structures on various surfaces evolves, the detailed chemical nature of the connection between the molecular and macro-scale worlds will become increasingly important. See, for example, Cahen, D.; Hodes, G. *Adv. Mater.* 2002, 14, 789 and Yaliraki, S. N.; Ratner, M. A. *Ann. N.Y. Acad. Sci.* 2002, 960, 153.

Recent advances in "wet" surface chemistry offer an increasingly sophisticated range of techniques for self-orienting molecular chemisorption on a wide variety of materials. See, e.g., Ullman, A., *Chem. Rev.* 1996, 96, 1533; see also, Buriak, J. M., *Chem. Rev.* 2002, 102, 1271; Seker, F.; Meeker, K.; Kuech, T. F.; Ellis, A. B.; *Chem. Rev.,* 2000, 100, 2505. Such techniques expand the broad, general applicability of synthetic chemistry to heterogeneous phase and have improved the prospects for "bottom up" fabrication strategies in nanotechnology. Specifically, work related to the construction of post-CMOS (complementary metal-oxide semiconductor) hybrid electronic devices using chemical techniques and molecular components to augment traditional fabrication techniques requires more control at the molecule/contact interfaces. Ideally, in the case of electronic devices employing conjugated organic molecules, a bond allowing strong electronic coupling between the energy bands of a bulk contact and the orbitals of a conjugated organic molecule would allow for a great deal of synthetic variation in device properties. Recent advances in surface chemistry offer an increasingly sophisticated range of techniques for orienting molecules on a wide variety of materials. See for example, Ullman, A. *Chem. Rev.* 1996, 96, 1533; Buriak, J. M. *Chem. Rev.* 2002, 102, 1271; and Seker, F.; Meeker, K.; Kuech, T. F.; Ellis, A. B. *Chem. Rev.* 2000, 100, 2505. These new techniques improve the prospects of future 'bottom-up' fabrication strategies in nanotechnology using chemical techniques and molecular components to augment traditional fabrication schemes. See, for example, Chen, J.; Reed, M. A.; Rawlett, A. M.; Tour, J. M. *Science* 1999, 286, 1550; Tour, J. M. *Acc. Chem. Res.* 2000, 33, 791; and Reed, M. A.; Chen, J.; Rawlett, A. M.; Price, D. W.; Tour, J. M. *App. Phys. Lett.* 2001, 78, 3735, all incorporated herein by reference.

In many experimental molecular electronic systems, molecules assembled between bulk metallic electrodes have chemical contacts that are highly polar, such as the sulfur-metal bond. This allows for undesired interfacial capacitance, possible electrochemical activity at the bond interface, and generally causes the molecule in the electrode gap to behave as a tunneling barrier. If the electronic properties of various chemical substituents on molecular devices are to be more fully exploited, a less polar, more electronically continuous chemical interface is required.

Some have attempted to functionalize surfaces with organic molecules employing various combinations of conditions and/or reagents.

U.S. Pat. No. 5,429,708 to Linford et al. provides for a method for producing a molecular layer of a selected molecular moiety on a silicon surface in which a silicon surface is etched to form a hydrogenated silicon surface and combined with a free radical-producing compound, where the free radical produced by the free radical-producing compound corresponds to the selected molecular moiety. The combined silicon surface and free radical-producing compound is then heated to sufficient temperature to initiate reaction between the free radical-producing compound and the hydrogenated silicon surface.

U.S. Pat. No. 6,284,317 B1 to Laibinis et al. relates to methods of derivatizing semiconductor surfaces, particularly porous silicon surfaces with silicon-carbon units. The derivatization occurs through the direct addition of an organometallic reagent in the absence of an external energy source such as heat and photochemical or electrochemical energies. The method of the invention allows the formation of unique intermediates including silicon hydride units bonded to metal ions. Because of these unique intermediates, it is possible to form previously inaccessible silicon-carbon units, for example where the carbon atom is an unsaturated carbon atom. Such inaccessible silicon-carbon units also include silicon-polymer covalent bond formation, in particular where the polymer is a conducting polymer. Thus, the present invention also provides a novel semiconductor surface/polymer junction having improved interfacial interactions.

U.S. Pat. No. 6,217,740 B1 to Andrieux et al. concerns a process for electrochemically producing a carbonaceous material with its surface modified by organic groups, in particular functionalized organic groups. The process comprises providing a solution, in a protic or aprotic solvent, comprising a salt of a carboxylate of an organic residue capable of undergoing a Kolbe reaction. The solution is then put in contact with a carbonaceous material, wherein the carbonaceous material is positively polarized with respect to a cathode that is also in contact with the solution. The solution may optionally contain an electrolyte. The invention also concerns carbonaceous materials modified at the surface with arylmethyl groups and the use of these modified materials, for example, in the production of composite materials.

U.S. Pat. No. 5,554,739 to Belmont discloses processes for preparing a carbon product having an organic group attached to a carbon material. The carbon material is selected from graphite powder, a graphite fiber, a carbon fiber, a carbon cloth, a vitreous carbon product, and an activated carbon product. In one process at least one diazonium salt reacts with a carbon material, in the absence of an externally applied electric potential, sufficient to activate the diazonium salt. In another process at least one diazonium salt reacts with a carbon material in a protic reaction medium.

U.S. Pat. No. 6,042,643 to Belmont et al. discloses processes for preparing a carbon black product having an organic group attached to the carbon black. In one process at least one diazonium salt reacts with a carbon black in the absence of an externally applied electric current sufficient to reduce the diazonium salt. In another process at least one diazonium salt reacts with a carbon black in a protic reaction medium. Carbon black products which may be prepared according to process of the invention are described as well as uses of such carbon black products in plastic compositions, rubber compositions, paper compositions, and textile compositions.

PCT Patent Application No. 03/032330 to Tour et al., filed on Jul. 26, 2002 and incorporated herein by reference, describes an electrical interconnect device achieved by applying to the surface of the contact(s) a molecular coating chosen from the group consisting of monomers, oligomers, or polymers that are primarily organic in origin, capable of forming self-assembled monolayers or self-assembled multilayers, electrically conducting or non-conducting, and contain metal-binding ligands as pendant groups or as part of their backbone.

*J. Phys. Chem. B* 1997, vol. 101, pp. 2415-2420 considers an electrochemical approach to derivatize atomically flat Si(111) surfaces with aryl adlayers. In particular, what is shown is that the electrochemical reduction of 4-nitro- and 4-bromobenzenediazonium salts in an aqueous acidic HF solution under applied external potential leads to modification of Si(111) surfaces.

*Polymer* 2003, vol. 44, pp 19-24 teaches that reduced polytetrafluoroethylene (PTFE) can be used to graft nitro and bromo-phenyl diazonium tetrafluoroborate salts in a manner similar to that used for carbon, except that no application of a reductive potential during grafting was required.

Notwithstanding the teachings of the prior art, the problem of making a high-quality molecule-surface interface that provides for a bond of sufficient strength and quality to effect good electronic or photonic interaction between an organic molecule and a surface remains less than completely solved. Moreover, a need remains for a method of making a high-quality molecule-surface interface using a minimum of additional steps, reagents or energy. Furthermore, it is believed that a direct covalent bond, allowing stronger electronic coupling between the energy bands of a bulk contact and the frontier orbitals of a conjugated organic molecule, would allow for a greater measure of synthetic variation in device properties and make contact effects less dominant. Furthermore, once the undesirable contact effects have been overcome, it is believed that a hybrid molecular electronic device can be constructed which can find various applications including those of switching, memory and sensing applications.

SUMMARY

The present invention discloses a method of making a molecule-surface interface comprising at least one surface and at least one organic group adjoined to the surface. The current method comprises contacting at least one organic group precursor with at least one surface wherein the organic group precursor is capable of reacting with the surface in a manner sufficient to adjoin the organic group and the surface.

According to the present invention, the surface defining the molecule-surface interface may be unadulterated or suitably derivatized if desired. Hydride passivation is a preferred surface derivatization according to some embodiments. According to other embodiments, the surface is curved and in the form of particles that are at least about 2 nm in average size.

Suitable materials of the current molecule-surface interface include those materials having a negative open circuit potential that is less than the reduction potential of the organic group precursor. Particularly preferred materials are selected from the group consisting of germanium, tin, boron, carbon, lead, gallium, arsenic, silicon, palladium, platinum, nickel, gold, copper, and any combination thereof. According to some embodiments, the material may be an alloy or a material that is doped with some compound or element. Suitable organic group precursors are preferably capable of reacting with the surface in a manner sufficient to adjoin the organic group and the surface. It is an advantage of the current method that no additional energy, reagents or steps are required to cause the organic group precursor to react with the surface to adjoin the organic group to the surface. In order for the organic group precursor to be capable of reacting with the surface it must have a reduction potential that is greater than the negative open circuit potential (OCP) of the surface. The organic group precursors of the present method are preferably diazonium salts and most preferably aryl diazonium salts depicted in formulas (IV), (V) and (VI):

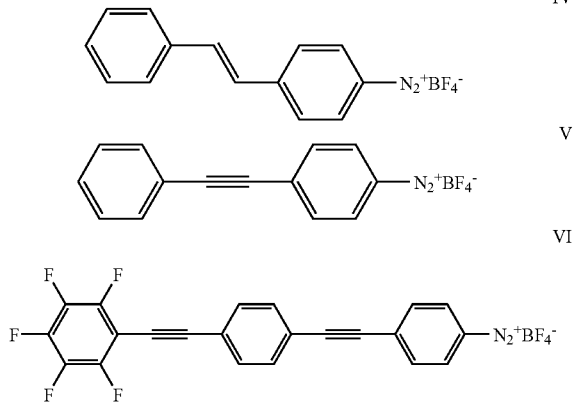

The present invention is also directed to a hybrid molecular electronic device. In one embodiment, a device in accordance with the present invention structurally resembles a conventional field effect transistor (FET), but differs in that the surface area between the source and drain is not protected with an insulating dielectric but is left open for attachment of molecules. In a preferred embodiment, the gate is moved from the top surface to the back of the wafer, although it is contemplated that the position of the gate is not critical, and that traditional architectures with the gate on the top side may be employed so long as the molecules can be grafted to the channel area. The device can be used as a switching device (i.e, a transistor), a memory element, or as a chemical sensor.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
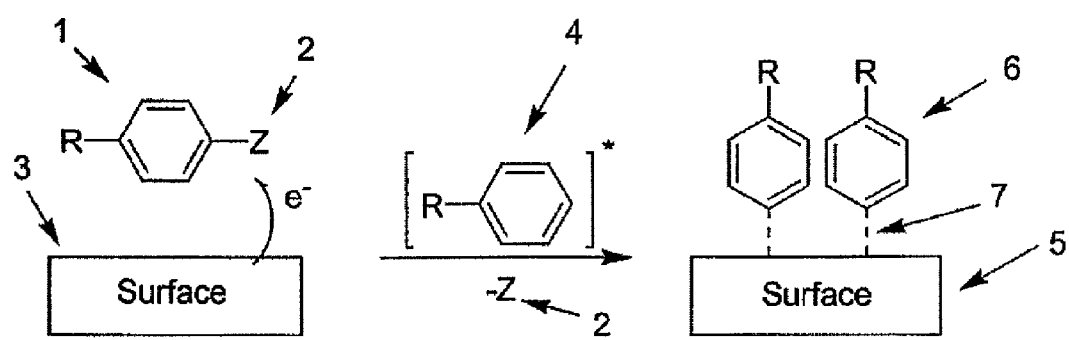
FIG. 1 presents a schematic illustration of a process whereby an organic group becomes adjoined to a reactant surface to provide a product surface.

In the following description, specific parametric details are set forth, including specific quantities, sizes, and the like, so as to provide a thorough understanding of embodiments of the present invention. However, it will be readily apparent to those of ordinary skill in the art that the present invention may be practiced while deviating to varying extents from specifically detailed parameters. In many cases, details concerning certain features and parameters of the invention have been omitted, inasmuch as such details are not believed to be necessary to obtain a complete understanding of the present invention and are within the skills of persons of ordinary skill in the relevant art.

The present invention comprises a method of making a molecule-surface interface wherein the interface comprises at least one surface comprising at least one material and at least one organic group adjoined to the surface. As used herein, adjoin will have its ordinary meaning; to wit, adjoin means to lie close to or to be in contact with one another. As further used herein, comprise shall mean to consist of in part. The current method comprises contacting at least one organic group precursor with at least one surface wherein the organic group precursor is capable of reacting with the surface in a manner sufficient to adjoin the organic group and the surface.

The surfaces of the current method preferably have those properties usually associated with surfaces used in surface science studies, but smooth surfaces are not essential. Thus, the subject surfaces should be clean, and free of or low in adsorbed contaminants or electrochemically inert oxide layers. Such surfaces are optimally prepared in oxygen-free, water-free environments to provide for clean, oxide-free surfaces. The surfaces will also be substantially smooth. It shall be understood, as it is to those in the art, that a smooth surface will still have a number of inherent defects at the nano-sized and atomic levels, such as, for example, kinks, ledges, terraces and the like. Techniques for preparing suitable subject surfaces may be found, for example, in *Mat. Res. Symp. Proc.* 1997, vol. 477, pp. 299-304, incorporated herein by reference.

According to one embodiment of the present invention, the surface is derivatized. As used herein, a derivatized surface is one that has been treated in such a manner as to have a modified surface composition. That is, the surface is combined with a reagent capable of chemically modifying the surface such that the outermost surface will comprise atoms or chemical groups different from the original surface composition. According to another embodiment, the derivatized surface is preferably a chemically passivated surface. As used herein, a passivated surface is one that has been substituted with some chemical species to mitigate or change the chemical reactivity of the surface. Passivation may, for instance, sufficiently reduce the reactivity of a metastable surface towards oxygen to preclude the formation of an oxide layer on the surface. In particular, according to another embodiment of the present invention, a derivatized surface is a passivated surface that is preferably at least partially hydride-passivated. A hydride-passivated surface shall be defined herein as a surface that is at least partially covered by hydrogen atoms chemically bonded to the surface. Methods of making a hydride-passivated silicon surface are well known in the art; exemplary methods may be found, for example, in *Appl. Phys. Lett.* 1990, vol. 12, pp. 656-658.

The surface of the current invention may have one or a combination of many different shapes. Preferably, the surface of the current invention has a shape that is flat, curved, corrugated, or a combination thereof. According to one embodiment, the surface is curved and in the form of particles that are at least about 2 nm in average diameter; more preferably between about 10 nm and about 250 nm in average diameter. Surfaces according to this embodiment may be known as nanoparticles and there exist methods to make such particles. See, for example, *Chem. Soc. Rev.* 1999, vol. 28 179-185, incorporated herein by reference. The surface may also be corrugated as would result from certain lithographic processes.

Surfaces may generally be characterized by an arrangement of atoms that may differ markedly from the arrangement of atoms in the bulk material beneath the surface. The precise arrangement of surface atoms is chiefly governed by the thermodynamics of the atomic packing; namely, the atomic arrangement that possesses the lowest total energy for the system will often tend to be the arrangement adopted by the surface atoms. Surfaces, though often possessing many defects and eluding complete characterization, are often envisioned as ideal surfaces with a perfectly regular arrangement of surface atoms. One way to describe such arrangements utilizes a vector notation wherein the spacing between atoms within a unit cell is defined by unit vectors. A detailed explanation of this vector notation description, called Miller indices, may be found in any standard reference on the subject, such as, for example, Anthony R. West, "Basic Solid State Chemistry", Wiley Press: New York, 1988, pp. 9-12. There are a nearly infinite number of suitable surface lattice configurations that are acceptable for use in the present invention. The precise surface, as described by the Miller index, will strongly depend on the material employed.

According to the present method, the surface shall comprise at least one material. The material of the present method will have a definite composition. There may be one or a combination of many materials that may have the desirable electronic properties required for use in the present method. In particular, those materials having a negative open circuit potential that is less than the reduction potential of the organic group precursor, as described in detail below, are suitable for use in the present method. However, some materials are more preferred than others. In particular, the material may be selected from the group consisting of transition metals, main group metals, Group IIIB elements, Group IVB elements, Group VB elements, and any combination thereof. By transition metals it shall be understood that these are the d-block metals denoted by Groups IIIA, IVA, VA, VIA, VIIA, VIIIA, IB, and IIIB according to the Previous IUPAC Form of The Periodic Table of the Elements as found in, for instance, the *CRC Handbook of Chemistry of Physics*, $82^{nd}$ Edition, 2001-2002 and used herein as the standard reference for all element group numbers throughout this specification. As used herein, the main group metals shall include the metals of Groups IA, IIA, IIIB, IVB, VB and VIB. Moreover, all elements of Groups IIIB, VB, and IVB, including for example carbon and boron, are included among the preferred materials of the present method. More preferred materials are selected from the group consisting of germanium, tin, boron, carbon, lead, gallium, arsenic, silicon, palladium, platinum, nickel, gold, copper, and any combination thereof; while most preferred materials are selected from the group consisting of silicon, gallium arsenide and palladium. According to one embodiment, a particularly preferred material of the current method is silicon.

The material of the current method may be a pure substance or a mixture of substances. Mixtures of substances can include alloys. However, it will be understood that no material can be absolutely pure and it is expected that the materials of the present method may contain trace contaminants. Indeed, in some embodiments of the current invention, it is desirable to employ mixtures or materials made intentionally impure, i.e. materials containing dopants. Thus, according to one embodiment, the material may be an alloy or a material that is doped with some compound or element, hereinafter referred to as a dopant. Typical dopants are well-known in the art; exemplary dopants include boron, phosphorus, arsenic, antimony, silicon, tellurium, zinc, aluminum, and chromium. At least one or more dopants may be added to the material of the present method to provide a material with desirable electronic properties. In particular, dopants are preferably added to provide materials that behave as semiconductors.

Materials with a broad range of electronic properties may be used in the current method including conductors, insulators, and semiconductors. The semiconductors of the present method may be those derived from the addition of any type of dopant or those not requiring the addition of a dopant. In particular, the semiconductor may be a p-type, n-type or intrinsic semiconductor. An intrinsic semiconductor will be defined herein as one that does not require the presence of a dopant to have the properties of a semiconductor.

The material of the present method may or may not be crystalline. A crystalline material may comprise one and often many single crystals. A single crystal comprises atoms arranged in a regular succession of repeating units, called unit cells, in a common direction and in a common lattice. The unit cell is the same for any one given crystal type. A regular succession of unit cells in a common direction gives rise to a single crystal. A crystalline material may comprise many individual crystals of the same type in different planes. A single material may have many different crystal types accessible to it. Thus, a single material comprising more than one crystal type is known as a polycrystalline material. A material without any detectable crystalline order is amorphous. It shall be understood that some materials may comprise microdomains of crystalline order that appear nearly amorphous according to current methods of crystal characterization, such as, for example X-ray diffraction (XRD). The current method can tolerate a wide range of crystalline or non-crystalline materials. In particular, a crystalline material may or may not be a single crystal. Furthermore, the material may be polycrystalline, nanocrystalline or amorphous.

There are materials according to the current method that are preferable with respect to the combination of crystallinity, dopants, conductivity and composition. According to some embodiments, preferred materials are palladium, gallium arsenide, p-type doped single-crystal silicon, intrinsic single-crystal silicon, n-type doped single-crystal silicon and n-type doped polycrystalline silicon. According to another preferred embodiment of the present invention, the material is silicon with a <100>, <111> or <110> surface. According to yet another preferred embodiment, the material is palladium, gallium arsenide, p-type doped single-crystal silicon, intrinsic single-crystal silicon, n-type doped single-crystal silicon or n-type polycrystalline silicon with a <100>, <111> or <110> flat, hydride-passivated surface.

The present method further comprises contacting at least one organic group precursor with at least one surface. The organic group precursor is preferably capable of reacting with the surface in a manner sufficient to adjoin the organic group and the surface. It is an advantage of the current method that no additional energy, reagents or steps are required to cause the organic group precursor to react with the surface to adjoin the organic group to the surface. In order for the organic group precursor to be capable of reacting with the surface, it must have a reduction potential that is greater than the negative open circuit potential (OCP) of the surface. OCP is defined as the "resting" potential of an electrode in the absence of an applied external potential. Reduction potential is defined as the energy change, expressed in volts (V), accompanying gain of an electron. See for example Xiaoge G. Zhang, "Electrochemistry of Silicon and its Oxides", Kluwer Publishers New York, 2001, pp. 1-43, incorporated herein by reference. Though not wishing to be bound by any particular theory, it is believed that the organic group precursor can undergo reduction and gain an electron from the surface when the negative open circuit potential is less than the reduction potential of the organic group precursor. According to this non-binding theory, a reactive intermediate is generated by reduction of the organic group precursor that is capable of reacting with the surface. It is believed that in this way the organic group may be adjoined to the surface in the present invention. As depicted in FIG. 1, an exemplary generic organic group precursor 1 comprising extrudable moiety 2 is reduced in the presence of reactant surface 3. Consequently, reactive intermediate 4 adjoins to product surface 5 to give adjoined organic group 6. Organic group 6 is depicted as adjoined to product surface 5 by a dashed line 7. As suggested by dashed line 7, the precise nature of the way in which organic group 6 is adjoined to product surface 5 is not completely known. Organic group 6 may be adjoined in any one of a number of ways including, but not limited to, a covalent bond, an ionic bond or a physisorbed bond. According to one preferred embodiment, the organic group is bonded to the surface via a covalent bond.

According to yet another embodiment of the present method, the organic group is arranged in at least one layer having at least some degree of order. Further according to this embodiment, it is believed that the organic groups may be arranged such that their long axis is between about 90° and about 45° to the surface. Furthermore, it is believed that the organic groups tend to arrange themselves such that the long axes of all the organic groups tend to be roughly parallel to each other. Thus, a layer that is formed is believed to be an ordered layer, although the degree of order will vary depending on the surface and the substrate, and order is not essential for many of the electrical and photonic processes eventually sought. It is also possible according to other embodiments of the current method, to assemble multiple layers upon the surface. Such layers will assemble upon the surface and further layers will tend to assemble upon preceding layers.

It is envisioned that there are many ways in which one could bring the organic group precursor into contact with the surface. For example, the organic group precursor may be in the form of a solution. Alternatively, it is conceivable that the organic group precursor could be brought into contact with the surface as a neat liquid or solid. It is even conceivable that a molecular beam could be used or that the substrate could be evaporated onto the surface by gas phase contact, for example. However, it is preferred according to the present invention to bring the organic group precursor into contact with the surface via a solution of the organic group precursor. Solvents for use in the present invention will be those capable of at least partially dissolving the organic group precursor. Preferred solvents include acetonitrile, methylene chloride, chloroform, ether, sulfolane, and in some cases, water. Acetonitrile is a most preferred solvent.

The organic group precursors of the present method will preferably be a diazonium salt. There exist an almost infinite number of diazonium salts that could be used in the present invention, including known diazonium salts that have been previously synthesized and new diazonium salts that have yet to be synthesized. Some exemplary classes of diazonium salts include alkyl and aryl diazonium salts. It will be appreciated that some diazonium salts will be more stable than others. While it is anticipated that, in theory, any diazonium salt may be used, according to one embodiment those that are stable to the required manipulations are particularly preferred. According to an alternative embodiment, those that are not particularly stable may be generated in situ from compounds that form diazonium salts when subjected to the proper conditions.

According to one embodiment, the diazonium salt is of the general formula (I) wherein $R_1$

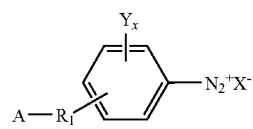

I may be alkyl, alkenyl, aryl, or alkynyl; A may be H, alkyl, alkenyl, aryl, alkynyl or any combination thereof; $Y_x$ may be at least one, and possibly more, substituents from the group consisting of nitro, amino, acyl, heteroatoms, alkyl, alkenyl, aryl, alkynl, fluoro, diazonium, diazo, allyl, thiol, thioacetate, isonitrile, nitrile and H; and $X^-$ may be any suitable counterion. In formula (I), it will be understood that the bond between $R_1$ and the aryl ring resides between two carbons of the aryl ring to indicate that $R_1$ may be in any position relative to diazonium moiety $N_2^+X^-$. It shall be further understood that in $R_1$, $Y_x$ and A, each alkyl, aryl, alkenyl and alkynyl group may be further substituted with other groups, such as fluoro, nitro, cyano, and amino. Moreover, alkyl, alkenyl and alkynyl groups are not limited to any particular length. The diazonium moiety of the diazonium salt comprises a latent molecule of $N_2$ and a counterion. Though not wishing to be bound by any particular theory, it is believed that, according to the present invention, the nitrogen of the diazonium salt is extruded as gaseous nitrogen when the reduction potential of the organic group precursor is greater than the negative open circuit potential of the surface and the resulting aryl radical permits for the organic group to be adjoined to the surface. The counterion of the diazonium salt affects the stability of the diazonium salt and is selected based on its ability to form a loose ionic bond with the charged dinitrogen moiety. Preferred counterions include tetrafluoroborate, tetrakis(pentafluorophenyl)-borate, hexafluorophosphate, chloride, bromide, iodide and hydrogensulfate. Tetrafluoroborate is a particularly preferred counterion for the diazonium salts of the current method.

More preferred diazonium salts are those according to general formula (II) wherein $Ar_1$ is

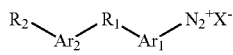

II at least one aryl group wherein the relative substitution pattern of the diazo group $N_2^+X''$ to $R_1$ may be ortho, meta or para and $Ar_1$ may be further substituted in any other position with at least one substituent selected from the group consisting of nitro, amino, acyl, heteroatoms, alkyl, alkenyl, aryl, alkynyl, fluoro, diazonium, diazo, allyl, thiol, thioacetate, isonitrile, nitrile and H; $R_1$ may be alkyl, alkenyl, aryl, or alkynyl of any further substitution and of any given length; $Ar_2$ is at least one aryl group wherein the relative substitution pattern of $R_2$ to $R_1$ may be ortho, meta or para and $Ar_2$ may be further substituted in any other position with at least one substituent selected from the group consisting of nitro, amino, acyl, heteroatoms, alkyl, alkenyl, aryl, alkynyl, fluoro, diazonium, diazo, allyl, thiol, thioacetate, isonitrile, nitrile and H; and $R_2$ is selected from the group consisting of alkyl, alkenyl, aryl, alkynyl and arylalkynl, of any further substitution and of any given length wherein arylalkynyl, by way of illustration, shall have the general formula (III); wherein $Y_x$ is at least one, and possibly more, substituents selected from

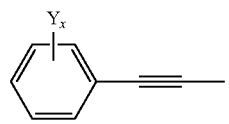

III the group consisting of nitro, amino, acyl, heteroatoms, alkyl, alkenyl, aryl, alkynyl, fluoro, diazonium, diazo, allyl, thiol, thioacetate, isonitrile, nitrile and H.

According to formula (II), it shall be understood that the relative substitution pattern of the diazo group $N_2^+X^-$ to $R_1$ on aryl group $Ar_1$ may be any relative substitution pattern including ortho, meta or para. Similarly, for aryl group $Ar_2$, the relative substitution pattern of $R_1$ and $R_2$ may be ortho, meta or para. Particularly preferred aryl diazonium salts for use in the present invention include those depicted in formulas (IV), (V) and (VI) and those shown in FIGS. 4a-4h.

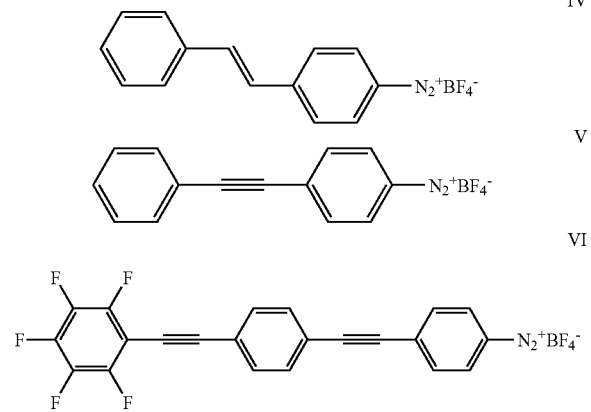

The diazonium salts of the present invention may be used directly as the organic group precursor. However, it is also possible according to an alternative embodiment of the present method to use another chemical species and obtain the organic group precursor in situ by adding, for example, another reagent. For example, it is conceivable that in the case of diazonium salts sufficiently unstable to permit for their isolation or manipulation, aromatic amines, also known as anilines, could be used in conjunction with a reagent such as isoamyl nitrite to provide an organic group precursor diazonium salt in situ.

Figure 2:
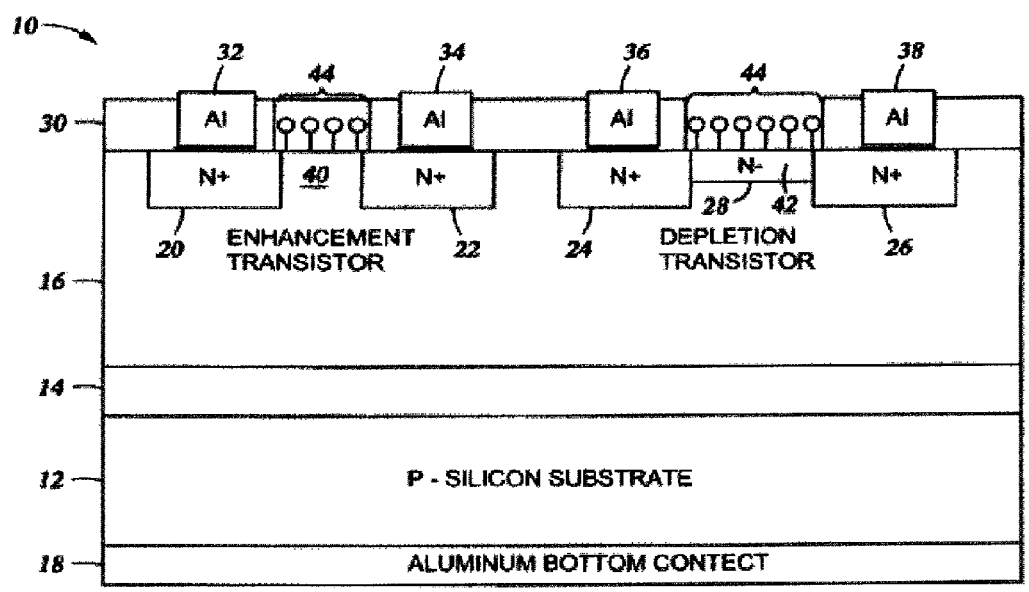
FIG. 2 is a cross section of a hybrid molecular electronic device in accordance with one embodiment of the invention.

In accordance with some embodiments of the present invention, FIG. 2 shows a hybrid molecular-electronic device 10. In the presently disclosed embodiment, device 10 is fabricated on a conventional silicon-on-insulator (SOI) wafer, although it is believed that the present invention is by no means limited to SOI wafers. The SOI wafer in the presently disclosed embodiment consists of a first silicon substrate 12, an insulating layer 14, and a second silicon substrate 16. SOI wafers such as shown in FIG. 2 are well-known and widely used in the semiconductor industry, and are commercially available from various sources.

The SOI substrate can be either p-type or n-type, depending on the majority carrier desired. As would be known by those of ordinary skill in the art, electrical conduction in a p-type substrate is due chiefly due to the movement of positive holes, wherein in an n-type substrate, electrical conduction is due chiefly to the movement of negative electrons. It is very common in semiconductor processing (e.g., complementary metal-oxide semiconductor or CMOS devices) to use both types of majority carriers by creating a "well" of one type in a substrate of the opposite type. Those of ordinary skill in the art having the benefit of the present disclosure will appreciate that the present invention can be practiced in the context of CMOS devices, although for the sake of clarity, the following description is limited to a device in a p-type substrate.

With continued reference to FIG. 2, device 10 further includes a metallization layer 18 on the underside of the SOI wafer, i.e., on the underside of substrate 12. As will hereinafter be described in further detail, metallization layer 18 serves as a contact to allow a potential to be placed on the substrate 12. Formation of metallization layers such as metallization layer 18 shown in FIG. 2 is a common semiconductor fabrication process.

A plurality of doped regions 20, 22, 24, and 26 each having a high concentration of n-type dopant (for example, without limitation, phosphorus, arsenic, or antimony), termed n+, are formed in substrate 16. These doped regions 20, 22, 24 and 26 are formed using conventional semiconductor fabrication techniques that are well-known and commonly practiced. The steps taken to form regions 20, 22, 24 and 26 as well as other common semiconductor fabrication techniques referred to herein, implicitly or explicitly, such as photomasking, etching, metallization, formation of oxide layers, metallization layers, and the like, will not be detailed herein, inasmuch as these techniques are abundantly well-known to those of ordinary skill in the art.

As will be hereinafter described, the n+ regions 20, 22, 24 and 26 can serve as transistor source/drains, and also provide ohmic contacts to the metallization.

Device 10 further comprises an insulating oxide layer 30 on the upper surface of substrate 16. Insulating layer 30 is selectively etched away to allow for the formation of metal (e.g., aluminum) contacts 32, 34, 36, and 38 contacting respective n+ source/drain regions 20, 22, 24, and 26. Insulating layer 30 is further etched away to expose channel regions 40 and 42 between respective source/drain pairs 20, 22 and 24, 26.

An area of lower dopant concentration, termed n−, designated with reference numeral 28 in FIG. 2, is formed to connect the n+ regions 24 and 26. This creates a path of continuity between these source/drain regions 24 and 26. It is contemplated that in one embodiment, the doping of region 28 may be limited to only the surface of substrate 16, resulting in an ultra-shallow channel region.

As thus far described, and as previously noted, device 10 is formed using conventional semiconductor fabrication techniques. To summarize, the fabrication process involves the following steps:

1) Cover the entire silicon-on-insulator (SOI) wafer (substrate 12, oxide layer 14, and substrate 16) with an insulating silicon oxide 30.
2) Open windows in the oxide and create highly doped, conductive pockets (20, 22, 24, and 26) in the silicon substrate 16 to serve as transistor source and drains.
3) Open another window which will allow doping of the same type but at a lower concentration (n− region 28). This will connect source/drain regions 24 and 26.
4) Define metal leads (32, 34, 36, and 38) which contact the source/drain areas and lead to large probe pads.
5) Define windows (channel regions 40 and 42) which stay open and allow molecular assembly after completion of the fabrication process.
6) Place metallization layer 18 on the wafer backside to contact the substrate.

In accordance with one aspect of the invention, a next step in the formation of device 10 is the grafting of a layer of molecules 44 to the surface of substrate 16 in the channel regions 40 and 42.

It is important to note that the embodiment of the invention shown in FIG. 2 permitted the inventors to rapidly test the concept of gate-property modulation via molecular attachment to the channel. However, it is to be understood that more standard architectures wherein the gate is set atop the channel can also be used so long as there are process steps allowing for attachment of molecules 44 to the channel. That is, those of ordinary skill in the art having the benefit of the present disclosure will appreciate that the present invention can be practiced in the context of more traditional CMOS device architectures.

In the preferred embodiment, grafting of the layer of molecules 44 to substrate 16 is accomplished through spontaneous activation of aryldiazonium salts to assemble covalently bound conjugated molecular layers on substrate 16. See: Stewart, M. P.; Maya, F.; Kosynkin, D. V.; Dirk, S. M.; Stapleton, J. J.; McGuiness, C. L.; Allara, D. L; Tour, J. M. "Direct Covalent Grafting of Conjugated Molecules onto Si, GaAs, and Pd Surfaces from Aryldiazonium Salts," *J. Am. Chem Soc.* 2004, 126, 370-378, which is hereby incorporated by reference herein in its entirety. In accordance with one aspect of the invention, molecular layer 44 may be a monolayer, a bilayer, or a multilayer, although a monolayer is the presently preferred embodiment.

Figure 3A:
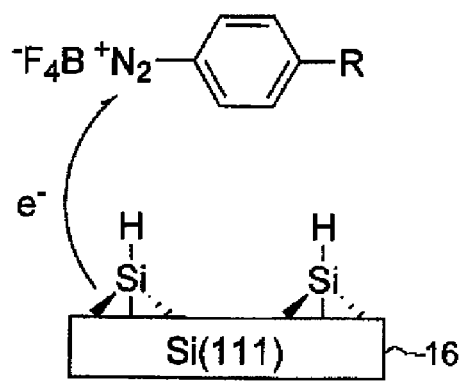
FIGS. 3a through 3e illustrate the chemical process of grafting molecules onto a silicon surface.
Figure 3B:
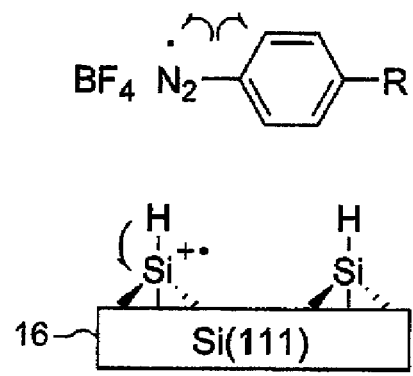
Figure 3C:
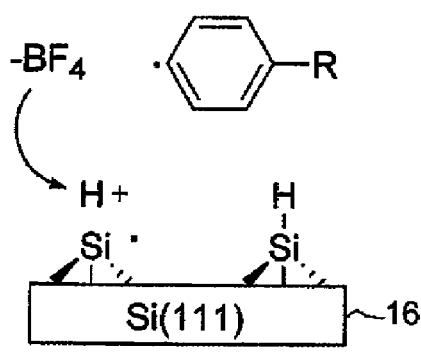
Figure 3D:
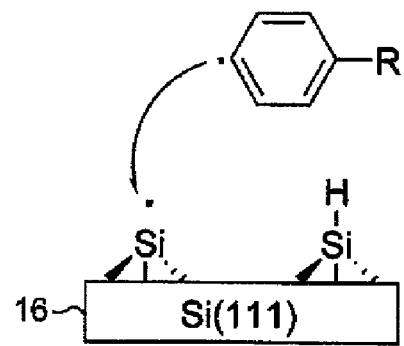
Figure 3E:
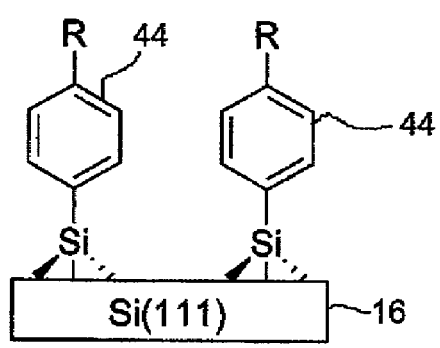

FIGS. 3a through 3e show an exemplary process by which molecules may be grafted onto a silicon surface using a diazonium salt. The procedure begins with hydride passivation of the silicon surface in channel regions 40 and 42, as shown in FIG. 3a. Thereafter, an electron transfer from the surface of substrate 16, at open circuit potential, generates a diazenyl radial, as shown in FIG. 3b, and then an aryl radical upon loss of $N_2$, as shown in FIG. 3c. The complementary oxidative process generates a proton, which eliminates as $HBF_4$, resulting in what is depicted in FIG. 3d. The result, shown in FIG. 3e, is a high-quality monolayer of molecules 44. The reaction has been shown to have a sensitivity to the presence of a radical scavenger such as butylated hydroxytoluene (BHT), added in small amounts to retard the formation of multilayers without preventing the reaction from occurring. Experimental data suggests that a high-quality monolayer of the chemisorbate molecules 44 tends to be complete within approximately two hours under nitrogen atmosphere.

A notable feature of the process described above with reference to FIGS. 3a through 3e is that it is performed at open-circuit potential (OCP), i.e., no externally applied activation potential is applied. This chemistry advantageously has the ability to be applied to devices where electrochemical means of surface activation are either unwieldy or impossible, such as isolated, non-planar, or low-conductive substrates.

FIGS. 4a through 4h are an exemplary sampling of the sorts of diazonium salts shown to be suitable for the purposes of the present invention. It is to be understood that the invention is by no means limited to those shown in FIGS. 4a through 4h. The diazonium molecules are first dissolved in anhydrous $CH_3CN$. When the device is immersed into the solution, the process as described above leads to formation of the molecular layer.

As shown in FIG. 2, two separate transistor-like devices are shown, a first including source/drain regions 20 and 22 and channel region 40, which is an enhancement mode device, and a second including source/drain regions 24 and 26 and channel region 42, which is a depletion mode device.

The following sets forth the inventors' present best understanding of the mechanisms by which the properties of channels 42 and 44 are modified as a result of the presence of molecules 44: In the depletion mode device, the molecules 44, with the proper gate bias applied to bottom contact 18, are at least partially reduced, gaining electrons. The molecules 44 will remain in this reduced form, even after removal of the gate bias. The negative charge on the molecules 44 will repel electrons from the n-region 28 at the surface, forming an immobile layer of fixed positive charge. This reduces the cross-sectional area for electron flow between source 24 and drain 26, through channel region 42, and therefore reduces the current between source 24 and drain 26. The application of voltage with the opposite polarity to gate contact 18 will oxidize the molecules 44 and return them to their original state. The removal of the molecular charge also restores the cross-sectional area in channel region 42. The current thus returns to its original magnitude. In some embodiments, the charge state of molecules 44 may be persistent to some extent, such that the device 10 may operate as a non-volatile, or at least semi-non-volatile memory cell. This device 10 can be operated as an n-channel depletion-mode molecular FET (mole-FET). It may be used as a two-level memory device by reading the current to determine if the molecules 44 are either oxidized or reduced. It is contemplated that multiple memory levels are also possible if the molecules 44 can take additional electrons.

The complementary device including source and drain regions 20 and 22 and channel region 40 is similar, but has no n− area corresponding to n− area 28 in the depletion mode device. The n+ source/drain regions 20 and 22 remain separated by the p-type substrate 16, and no current flows between them. By applying the proper gate bias to gate contact 18, the assembled molecules 44 are at least partially oxidized and become positively charged. This attracts electrons to the surface, creating a channel which connects source 20 to drain 22 and allows current flow. The application of voltage with the opposite polarity will reduce molecules 44 and return them to their original state. The device functions like an n-channel enhancement-mode molecular FET, and can serve as a memory similar to the depletion-mode device.

It is contemplated that the mole-FET, both depletion and enhancement modes, may also be used as a chemical sensor. When a molecule to be detected, called the target molecule, reacts with an appropriately-chosen chemically bonded molecule, this reaction removes the bound molecule or alters its reduction/oxidation properties. As with application of a gating voltage to metallization layer 18, this modulation of the reduction/oxidation properties of the molecules 44 results in a corresponding modulation of the conductivity across channel regions. The resulting change in resistance is an indicator of the presence of the target molecule.

It is contemplated, for example, that certain chemical or biological agents may be sensed through the use of saccharides, polypeptides, biotin or oligonucleotides (i.e. DNA) as the grafted molecules. Upon exposure to analytes that are complements to the bonded molecules, such as cell wall saccharides, peptide substrates, biotin conjugates (avidin), complementary DNA strands, respectively, the oxidation/reduction or electrostatic properties of the grafted molecules will alter, thereby modulating the channel charge or partial charge. This modulation should be detectible via the source-drain-gate electronic characteristics. Those of ordinary skill in the art will appreciate that the use of molecules as a memory element or sensor greatly simplifies fabrication of such devices. The process of attaching molecules 44 can be performed in a simple laboratory hood instead of requiring an expensive semiconductor cleanroom. Further, since a small physical area may contain a relatively large number of bonded molecules, devices in accordance with the present invention are reduced in size relative to alternative technologies.

Figure 5:
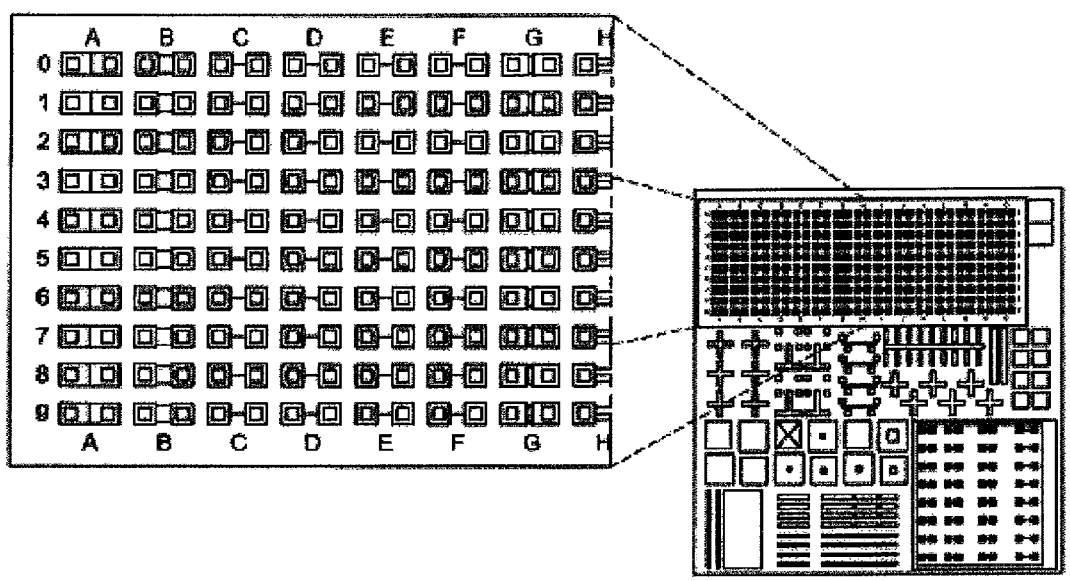
FIG. 5 is a schematic of a wafer of hybrid molecular electronic devices fabricated in accordance with one embodiment of the invention.

FIG. 5 shows an example of some exemplary mole-FET devices fabricated on a six-inch SOI wafer. Each wafer has approximately 190 die sites. On each die, there are approximately 150 mole-FET devices covering systematic variations of channel length, channel width, width/length ratio, and parameters related to the area of grafted molecules, such as area length, area width, overlap, and so on. Experimentally, devices have been fabricated with channels as small as 1 μm long and 1 μm wide and as large as 100 μm long and 100 μm wide, although the present invention is in no sense limited to channels and other design parameters within such specified ranges. Variations in substrate types (p-type or n-type), doping levels, channel silicon thickness, gate oxide thickness, and so on, are also contemplated as falling within the scope of the invention.

The programming of some types of non-volatile memory, such as flash memory, require the use of a relatively high voltage (>10 volts), which limits lifetime. The programming voltage of devices such as device 10 described herein has been experimentally proven to be less than 5 volts. Furthermore, as the devices are made smaller, the application voltages will decrease. Likewise, as the devices become smaller, the surface area to volume of the channels becomes greater, therefore the electronic impact of the grafted molecules should be more profound on smaller devices.

Figure 6A:
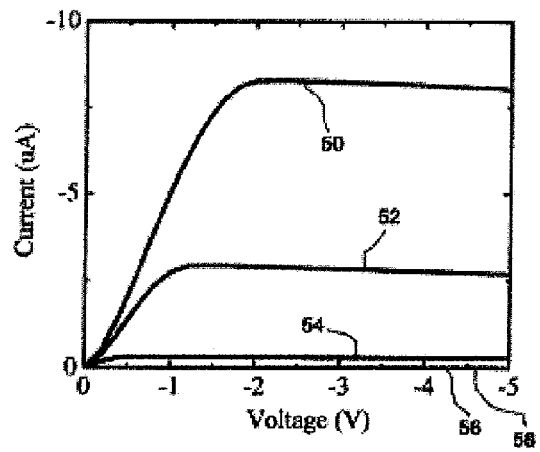
FIGS. 6a and 6b are current-voltage plots of a hybrid molecular electronic device in accordance with one embodiment of the invention respectively having molecules grafted to the gate region (FIG. 6a) and molecules removed from the gate region (FIG. 6b)
Figure 6B:
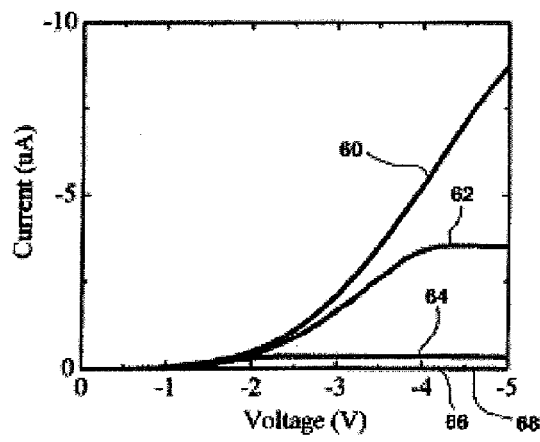

With mole-FET devices such as have thus far been described herein, the effects of the grafting of molecules 44 to gate regions 40 and 42 can be clearly observed. FIGS. 6a and 6b are current-voltage plots of a hybrid molecular electronic device in accordance with one embodiment of the invention respectively having molecules grafted to the gate region (FIG. 6a) and molecules thereafter removed from the gate region (FIG. 6b). The device of FIG. 6a was fabricated like device 10 described above with the molecule shown in FIG. 4g attached to the channel region 42. A well-defined transistor output characteristic (I-V curve) can be clearly observed. In particular, shown in FIG. 6a are the I-V curves corresponding to gate voltages of −20 V (curve 50), −15 V (curve 52), −10 V (curve 54), −5 V (curve 56), and 0 V (curve 58). Molecules 44 were then removed from the experimental device, through 15 minutes of exposure to UV ozone treatment, which destroys the molecules 44 but has little effect on the device's inorganic base structure, other than creating a surface oxide. FIG. 6b shows the performance of the resultant molecule-free device, for gate voltages of −20 V (curve 60), −15 V (curve 62), −10 V (curve 64), −5 V (curve 66), and 0 V (curve 68).

Those of ordinary skill in the art having the benefit of the present disclosure can further appreciate the effect of the grafted molecules 44 though observation of the relationship of channel current to molecule area. Referring to FIG. 7, at a constant gate voltage of −20 V, the I-V characteristics of five transistors which are identical except for the area for molecule grafting is varied.

Figure 7A:
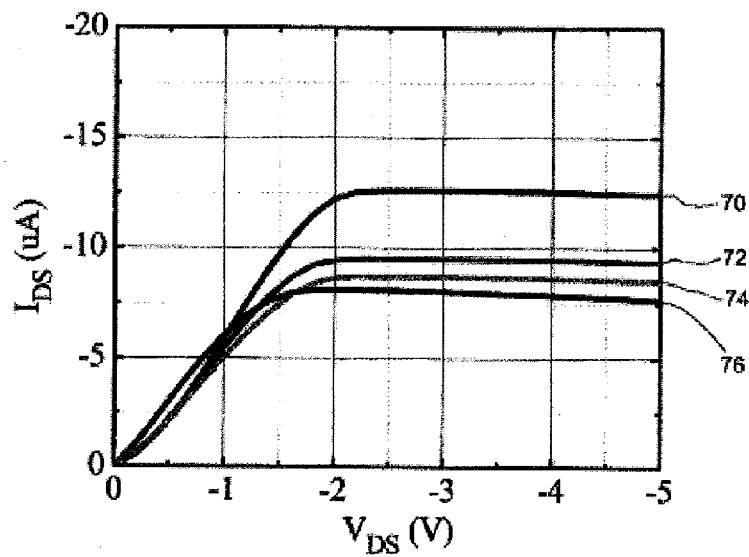
FIG. 7a is a current-voltage plot of devices in accordance with one embodiment of the invention for molecule grafting areas of varying dimensions, showing that current scales with grafting area.
Figure 7B:
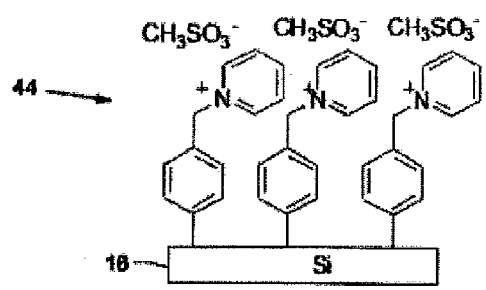
FIG. 7b illustrates a portion of the device 10 utilized to derive the data plotted in FIG. 7a, including a portion of the substrate and a molecular monolayer thereon.

In each case in FIG. 7a, the molecule layer 44 is a molecular monolayer as shown in FIG. 7b, which is formed using the diazonium salt from FIG. 3h, resulting in the grafting of benzyl alcohol to silicon substrate 16, followed by further treatment with methanesulfonyl chloride ($CH_3SO_2Cl$) and pyridine to form the layer 44 shown in FIG. 7b. While the area of the channel remains the same, the nominal molecules grafted area upon the channel varies from 85×85 $\mu m^2$ (I-V curve 70 in FIG. 7), to 60×60 $\mu m^2$ (I-V curve 72), to 35×35 $\mu m^2$ (I-V curve 74), to 20×20 $\mu m^2$ (I-V curve 76). As can be seen in FIG. 7a, the channel current decreased steadily with decreasing molecule-grafted area. Since all other design parameters are the same, including channel size, this effect must be credited to the molecular effect of molecules 44.

Figure 4A:
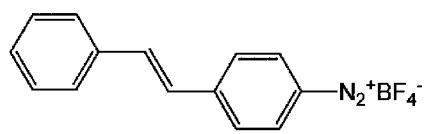
FIGS. 4a through 4h are exemplary candidate molecules for incorporation into the device of FIG. 2.
Figure 4B:
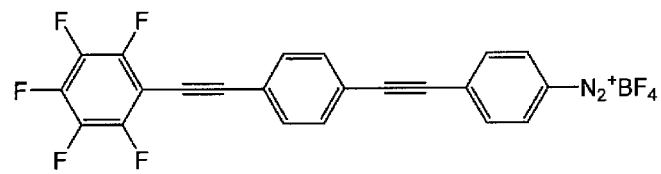
Figure 4C:
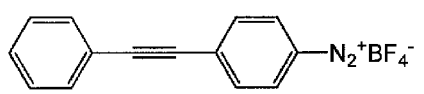
Figure 4D:
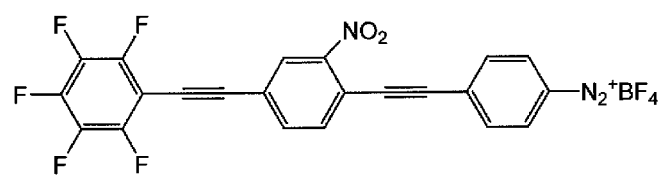
Figure 4E:
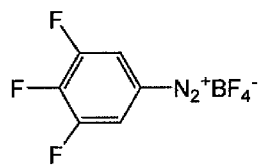
Figure 4F:
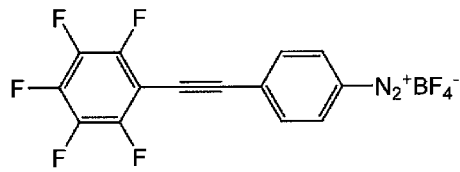
Figure 4G:
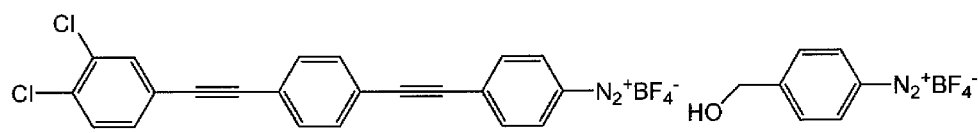
Figure 4H:
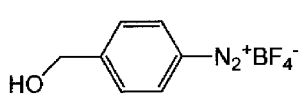
Figure 8:
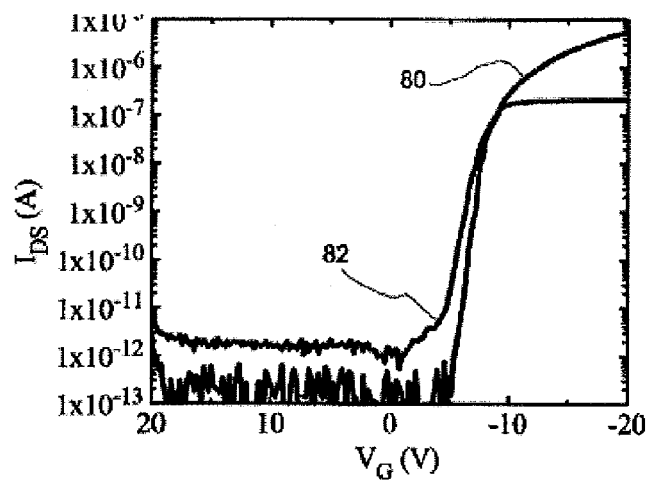
FIG. 8 is a current-voltage plot of a device in accordance with one embodiment of the invention showing the effects of varying gating voltages thereon when molecules are grafted over a channel region of the device and when these molecules have been removed from the same device.

The influence of molecular monolayer 44 is also shown through observation of gating effects. As shown in FIG. 8, a device 10 in accordance with the presently disclosed embodiment of the invention, using molecules as shown in FIG. 4g, was tested with a source-drain voltage of −1.5 V, resulting in the I-V curve 80. Then, molecular monolayer 44 was removed using 15 minutes of UV ozone treatment, removing grafted molecules 44 but introducing little change to the backbone transistor structure. Further testing resulted in the I-V curve designated with reference numeral 82 in FIG. 8. As would be appreciated by those of ordinary skill in the art, there are clear differences in corresponding gating characteristics. Firstly, the saturation channel current for the molecule-bearing device was much larger than that of the molecule-absent transistor (approximately two orders of magnitude). Therefore, the molecule-bearing device has a much larger on/off ratio. Secondly, the sub-threshold swing for the molecule-bearing device was better than the molecule-absent device.

Figure 9:
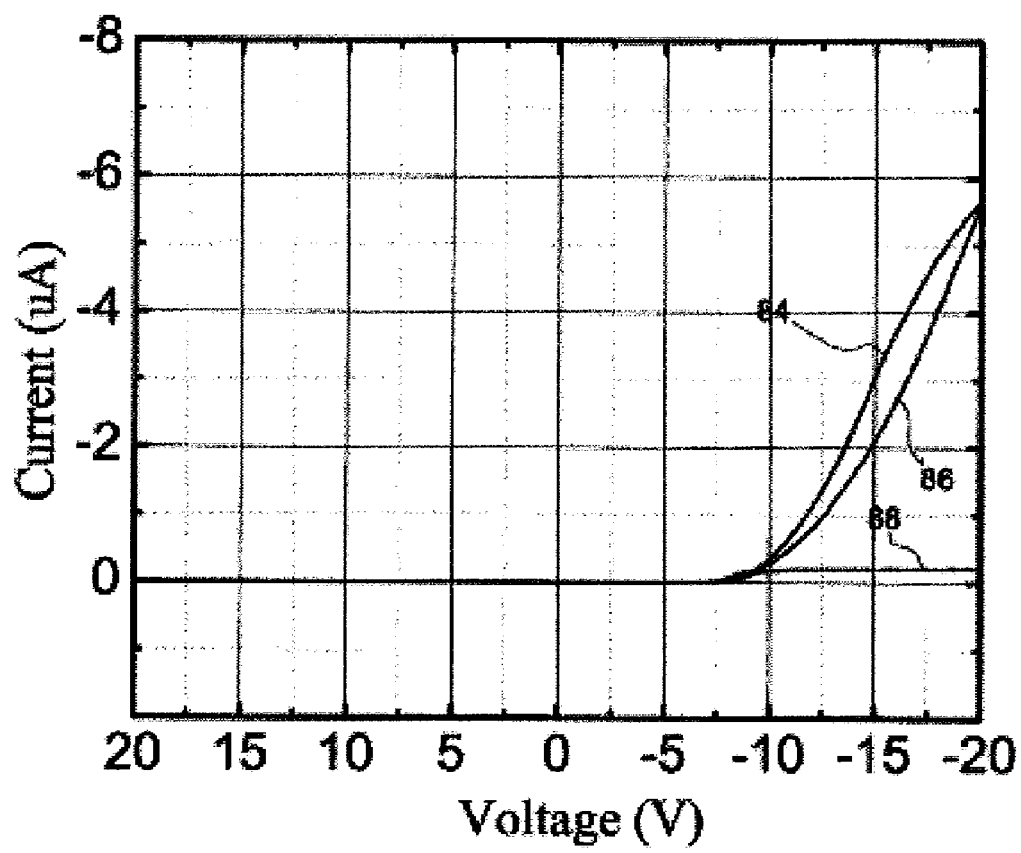
FIG. 9 is a current-voltage plot of a device in accordance with one embodiment of the invention showing the effects of molecules being grafted onto a gate portion thereof as compared with such molecules being removed from the gate portion.

A further example illustrating the effects of grafting molecules 44 onto the gate region (40 or 42) of the device of FIG. 2 is shown in FIG. 9, which uses molecules 44 corresponding to those shown in FIG. 7b. As shown in FIG. 9, in the presence of grafted molecules 44, channel current increases significantly (I-V curves 84 and 86 in FIG. 9) as compared with that where molecules 44 are not present (I-V curve 88 in FIG. 9). Note that 86 is the forward sweep direction (0 to −20 V) and 84 is the backward sweep direction (−20 to 0 V) for the molecule-grafted device. Clearly, the grafting of molecules 44 exerts significant influences on the device's input and output characteristics.

The hysteresis effect observable between curves 84 (voltage scanning down) and 86 (voltage scanning up) in FIG. 9 (falling voltage versus rising voltage) indicates a memory effect. It is contemplated that such hysteresis can be increased, possibly leading to a non-volatile memory.

In an alternative embodiment of the invention, a conductive layer of silicon or other material is placed in the silicon under the transistor to serve as the gate instead of locating it on the backside. This allows easier programming of individual devices. Also regular silicon wafers can be used in place of SOI wafers.

Furthermore, a traditional MOS transistor structure can be used if the gate oxide is removed by an etching process, allowing molecules to attach to the silicon under the gate. A traditional MOS transistor structure could be used and an opening could be made to the gate. Molecules would then assemble directly to the top of the gate.

From the foregoing description of particular embodiments of the invention, it should be apparent that a hybrid molecular electronic device has been disclosed which may be operable as switching, memory, and/or sensor device has been disclosed which offers significant and unique properties over present technologies. Although a broad range of implementation details have been discussed herein, these are not to be taken as limitations as to the range and scope of the present invention. A broad range of implementation-specific variations and alterations from the disclosed embodiments, whether or not specifically mentioned herein, may be practiced without departing from the spirit and scope of the.

For example, although specific techniques have been described herein for formation of the molecular monolayer 44 on the channel region of device 10, the present invention is in no sense limited to these specific techniques, and it is contemplated that various alternative methods may be employed to achieve the molecular modulation of device operation as described herein.

Furthermore, although the present invention has been described herein in the context of silicon devices, it is contemplated that the present invention may find applicability in the context of other materials, including, without limitation, gallium arsenide devices, as the molecular attachment chemistry is quite broad. Also, as noted above, it is contemplated that the invention is in no sense limited to devices in which the gating voltage is applied to the underside of the substrate, and that those of ordinary skill in the art having the benefit of the present disclosure would appreciate that more conventional field-effect transistor architectures may be adapted to achieve the benefits and results of the present invention.

Finally, although specific explanations as to how the presence of molecules 44 on the channel regions affects the conductive properties of the channels (oxidation and reduction of the molecules) have been presented herein, it is to be understood that such explanations are only the inventors' present best theoretical understanding of the electrochemical mechanisms involved, based upon empirical observations; it is not intended that the present invention be limited by the accuracy of such explanations. For example, it could be that the electrostatic potential of the molecules atop the channel affects the mobility within the channel.

Experimental Examples

Reagents and Solvents for Surface Reactions

Acetonitrile (99.5+%) for surface reactions was purchased from Aldrich packed under nitrogen in a SureSeal container. Acetonitrile, $CH_2Cl_2$, ethanol, and water used for rinsing were purchased at HPLC grade and used without further purification. Concentrated ammonium fluoride was purchased at VLSI grade from J. T. Baker. Concentrated hydrochloric acid, concentrated sulfuric acid, 49% hydrofluoric acid, and 30% hydrogen peroxide were purchased at reagent grade. Before use, all diazonium salts were stored under nitrogen in tightly capped vials, in the dark at $-30°$ C.

Ellipsometric Measurements

Measurements of surface optical constants and molecular layer thicknesses were taken with a single wavelength (632.8 nm laser) Gaertner Stokes Ellipsometer.

Cyclic Voltammetry (CV) Measurements.

Electrochemical characterization was carried out with an Bioanalytical Systems (BAS CV-50W) analyzer. The reference was a saturated calomel electrode (SCE). The counterelectrode was a clean Pt wire. The aqueous redox couple and electrolyte were 0.01 M $Fe(CN)_6^{3/4-}$ in 0.1 M $KClO_4$. Approximately 1 $cm^2$ of sample was exposed to solution during CV measurements. The scan rate was 100 mV $s^{-1}$ from $-200$ mV to 600 mV.

X-Ray Photoelectron Spectroscopy (XPS) Measurements

A Physical Electronics (PHI 5700) XPS/ESCA system at $5 \times 10^{-9}$ torr was used to take photoelectron spectra. A monochromatic Al X-ray source at 350 W was used with an analytical spot size of 1.2 mm and 45 degree takeoff angle.

FTIR Measurements

A customized analytical system, based on a Mattson Research Series bench, was used, whose basic details are described elsewhere, see Parikh, A. N.; Allara, D. L. *J. Chem. Phys.* 1992, 96, 927, incorporated herein by reference. FTIR spectra were obtained under an extended dry air purge using a liquid $N_2$ cooled wide-band MCT detector. External reflection spectra used 600 scans at 2 $cm^{-1}$ resolution at an 88.5 degree angle of incidence. Transmission spectra used 600 scans at 4 $cm^{-1}$ resolution at normal incidence. A multi-point baseline correction and $H_2O$ and $CO_2$ subtractions in GRAMS/32 are used for qualitative and presentation purposes.

Surface Preparation and Optical Constants

Pd samples were deposited by ion mill sputtering onto a 2-inch undoped oxidized Si wafer at 0.1 Å $s^{-1}$ until a final thickness of 2000 Å was reached. No surface adhesion layer was used. The Pd samples were reacted within 10 minutes after coming out of the vacuum chamber, without any surface cleaning. The n value for the clean Pd surface was 1.9 and k was $-4.2$. Highly doped 2-inch n-type Si(111) wafers (prime grade, As doped, 0.001-0.005 ohm-cm) were first cleaned for 20 minutes in 2:1 $H_2SO_4/H_2O_2$ "piranha solution" followed by rinsing copiously with water and drying in a stream of $N_2$. The wafer was then hydride-terminated by immersion in $N_2$-sparged concentrated (40%) ammonium fluoride for 15 minutes, rinsed with water, and dried in a stream of $N_2$. The n value for the Si(111):H surface was 3.87 and k was $-0.04$. Undoped GaAs(100) samples were cut (about 4 $cm^2$) from a 3-inch wafer, sonicated in ethanol for 15 minutes, and UV/$O_3$ cleaned for 15 minutes. The oxidized GaAs shards were then treated with concentrated (37%) HCl for 1 minute, followed by a brief rinse in water, then ethanol, and then a gentle stream of $N_2$. The n value for the clean GaAs surface was 3.85 and k was $-0.2$. XPS experiments on GaAs used shards from a lightly Te-doped GaAs(100) wafer prepared and characterized with the same protocols.

General Procedure for the Coupling of a Terminal Alkyne with an Aryl Halide Utilizing a Palladium-copper Cross-Coupling (Castro-Stephens/Sonogashira Protocol)

To an oven-dried screw cap tube or a round bottom flask equipped with a magnetic stir bar were added the aryl halide, bis(triphenylphosphine) palladium(II) dichloride (1-5 mol % based on aryl halide), and copper(I) iodide (1-5 mol % based on aryl halide). The vessel was then sealed with a rubber septum, evacuated and backfilled with nitrogen thrice. Triethylamine or N,N-diisopropylethylamine (Hünig's base) was added followed by THF serving as a co-solvent. After a 5-minute incubation at room temperature, the terminal alkyne was then added and the reaction mixture stirred until complete. External heating up to 80° C. was used for sluggish reactions. The reaction vessel was cooled to room temperature and quenched with water or a saturated solution of $NH_4Cl$. The organic layer was diluted with methylene chloride and washed with a saturated solution of $NH_4Cl$ until the blue color of copper complexes could not be seen in the aqueous phase. The combined aqueous layers were extracted with methylene chloride thrice. The combined organic layers were dried over anhydrous $MgSO_4$ and the solvent removed in vacuo. The crude product was then purified by flash or column chromatography (silica gel). Alternative work-up procedure consisted of solvent removal in vacuo directly followed by chromatography.

General Procedure for the Diazotization of Aromatic Amines with Nitrosonium Tetrafluoroborate in the Acetonitrile-Sulfolane System The nitrosonium salt was weighed out in a nitrogen filled dry box and placed in a round bottom flask equipped with a magnetic stirring bar and sealed with a septum. Acetonitrile and sulfolane were injected in 5 to 1 volume ratio and the resulting suspension was cooled in a dry ice-acetone bath to −40° C. The solution of the aromatic amine was prepared by adding warm sulfolane (45-50° C.) to the amine under a nitrogen blanket, sonication for 1 minute and subsequent addition of acetonitrile (10-20% by volume) and added to the nitrosonium salt suspension over 10 minutes. The reaction mixture was kept at −40° C. for 30 minutes and let warm up to the room temperature. At this point the diazonium salt was precipitated by the addition of ether, collected by filtration, washed with ether and dried. Additional purification of the salt was accomplished by re-precipitation from DMSO by dichloromethane and/or ether.

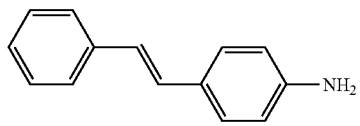 [SMILES: Nc1ccc(/C=C/c2ccccc2)cc1]

4-styrylphenylamine

4-Iodoaniline (4.380 g, 20.0 mmol), styrene (2.78 mL, 24.0 mmol), palladium(II) acetate (0.244 g, 1.0 mmol), potassium carbonate (2.488 g, 18.0 mmol), tetrabutylammonium bromide (9.348 g, 29.0 mmol), and DMF (25 mL) were coupled according to the general Heck coupling procedure above for 4 h at 100° C. The crude product was purified via flash column chromatography (3:7 ethyl acetate:hexanes) yielding 2.203 g (56%) of a light brown solid. IR (KBr) 3446.8, 3361.6, 3198.4, 1605.0, 1506.7, 1437.9, 1280.4, 1173.2, 1065.7, 965.8, 814.8, 749.1, 685.7, 525.6, 484.5 $cm^{-1}$. $^1H$ NMR (400 MHz, $CDCl_3$) δ7.54-7.52 (m, 2H), 7.41-7.37 (m, 3H), 7.27 (tt, J=7.6, 1.6. Hz, 1H), 7.09 (d, J=16.4 Hz, 1H), 6.98 (d, J=16.4 Hz, 1H), 6.71 (dt, J=8.8, 2.4 Hz, 2H), 3.77 (br s, 2H). $^{13}C$ NMR (100 MHz, $CDCl_3$) δ 146.61, 138.40, 129.14, 129.05, 128.44, 128.20, 127.34, 126.56, 125.53, 115.65.

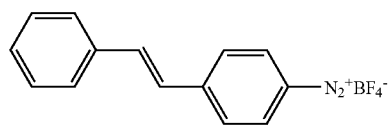

4-styrylbenzenediazonium tetrafluoroborate

To a 25 mL round bottom in a drybox was added nitrosonium tetrafluoroborate (0.11 g, 0.95 mmol). Acetonitrile (2 mL) was added and the flask was cooled down to −30° C. A solution of 4-STYRYLPHENYLAMINE (0.17 g, 0.86 mmol) and BHT (0.19 g, 0.86 mmol) in acetonitrile (5 mL) was added dropwise via syringe. The reaction was allowed to warm to −5° C. over 20 min. Ether (10 mL) was then added and the precipitate was filtered. The title compound was purified by re-precipitating from acetonitrile (3 mL) with ether (15 mL) to yield 0.82 g (34%) of the desired compound.

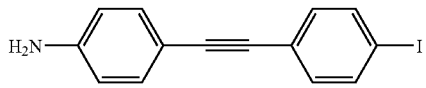

4-(4-iodophenylethynyl)aniline 1,4-Diiodobenzene (4.95 g, 1.0 mmol), bis(triphenylphosphine)palladium(II) dichloride (0.07 g, 0.10 mmol), copper (I) iodide (0.019 g, 0.10 mmol), triethylamine (5 mL), THF (10 mL) and 4-ethynylaniline 0.585 g, 5.00 mmol) were used following the general procedure for couplings. For the synthesis of 4-ethynylaniline, please see Tour et al. *Chem. Eur. J.* 2001, vol. 7, pp. 5118-5134 incorporated herein by reference. The tube was capped and stirred room temperature for 12 h. Flash column chromatography ($CH_2Cl_2$—hexanes as eluent) afforded the desired product as light yellow needles (1.13 g, 71% yield). IR (KBr) 3441, 3356, 2210, 1612, 1515, 1281, 1135, 1003, 842, 811, 512 $cm^{-1}$. $^1H$ NMR (400 MHz, $CDCl_3$) δ 7.650 (m, AA' part of AA'XX' pattern, J=8.7, 2.4, 1.8, 0.7 Hz, 2H), 7.324 (m, XX' part of AA'XX' pattern, J=8.7, 2.4, 1.8, 0.7 Hz, 2H), 7.208 (m, AA' part of AA'XX' pattern, J=8.6, 2.4, 1.8, 0.6 Hz, 2H), 6.630 (m, XX' part of AA'XX' pattern, J=8.6, 2.4, 1.8, 0.6 Hz, 2H), 3.833 (s, 2H). $^{13}C$ NMR (100 MHz, $CDCl_3$) δ 147.05, 137.60, 133.20, 133.07, 123.67, 114.95, 112.39, 93.45, 91.83, 86.69.

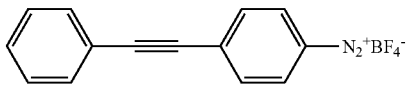

4-phenylethynylbenzenediazonium tetrafluoroborate

Following the general diazotization procedure 4-phenylethynylaniline (0.579 g, 3.00 mmol) was treated with $NOBF_4$ (0.368 g, 3.15 mmol) in pure acetonitrile (20 mL). For the synthesis of 4-phenylethynylaniline, please see Kosynkin et al. *Org. Lett.* 2001, vol. 3, pp. 993-995, incorporated herein by reference. Yellow needles of the desired product were precipitated with ether (0.753 g, 86.1% yield). IR (KBr) 3101, 2294, 2217, 1578, 1415, 1033, 1071, 845, 692 $cm^{-1}$. $^1H$ NMR (400 MHz, $CD_3CN$) δ 8.86 (m, AA' part of AA'XX' pattern, J=8.7, 2.4, 1.7, 0.5 Hz, 2H), 8.16 (m, XX' part of AA'XX' pattern, J=8.7, 2.4, 1.7, 0.5 Hz, 2H), 7.49-7.59 (m, 3H), 7.67-7.71 (m, 2H). $^{13}C$ NMR (100 MHz, $CD_3CN$) δ 137.15, 134.67, 134.06, 133.13, 131.45, 129.82, 121.96, 114.35, 101.58, 88.21.

2

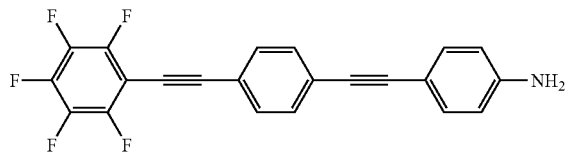

4-(4-iodophenylethynyl)aniline (aniline 2)

(0.319 g, 1.0 mmol), bis(triphenylphosphine)palladium(II) dichloride (0.028 g, 0.04 mmol), copper(I) iodide (0.008 g, 0.04 mmol), triethylamine (2 mL), THF (2 mL) and pentafluorophenylacetylene (0.288 g, 1.50 mmol) were used following the general procedure for couplings. The tube was capped and stirred room temperature for 14 h. Flash column chromatography ($CH_2Cl_2$—hexanes as eluent) afforded the desired product as light yellow needles (0.165 g, 43% yield). IR (KBr) 3442, 3347, 2959, 2163, 2142, 1629, 1552, 1518, 1352, 1332, 1281, 1247, 1166, 838 cm$^{-1}$. $^1$H NMR (400 MHz, CDCl$_3$) δ7.47-7.54 (m, 4H), 7.343 (m, XX' part of AA'XX' pattern, J=8.7, 2.5, 1.8, 0.6 Hz, 2H), 6.640 (m, XX' part of AA'XX' pattern, J=8.7, 2.5, 1.8, 0.6 Hz, 2H), 3.859 (s, 2H). $^{13}$C NMR (100 MHz, CDCl$_3$) δ 147.23, 133.32, 131.97, 131.88, 131.52, 125.60, 120.58, 114.93, 112.22, 93.30, 87.18, 74.66. $^{19}$F NMR (470.5 MHz, THF-d$_8$) δ −134.73-134.80 (m, 2F), −151.38 (tt, J=21, 3 Hz, 1F), −160.51-160.62 (m, 2F).

VI

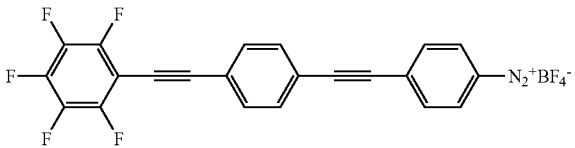

Diazonium Salt VI

Following the general diazotization procedure, ANILINE 2 (0.153 g, 0.040 mmol) was treated with NOBF$_4$ (0.052 g, 0.52 mmol) in acetonitrile (4 mL) and sulfolane (4 mL). The precipitation of the product was effected by the addition of ether (150 mL). The salt was washed with ether and dried in vacuo (0.124 g, 64% yield). IR (KBr) 3106, 2275, 2214, 1576, 1526, 1502, 1078, 989, 854, 832 cm$^{-1}$. $^1$H NMR (400 MHz, DMSO-d$_6$) δ 8.71-8.74 (m, 2 μl), 8.15-8.17 (m, 2H), 7.74-7.79 (m, 4H). $^{13}$C NMR (100 MHz, DMSO-d$_6$) δ 133.87, 133.63, 133.09, 132.64, 132.25, 122.11, 114.93, 100.15, 98.31, 89.83, 75.57. $^{19}$F NMR (470.5 MHz, CD$_3$CN) δ −136.86-136.92 (m, 2F), −150.42 ($^{10}$BF$_4$), −150.47 ($^{11}$BF$_4$), −152.72 (tt, J=21, 3 Hz, 1F), −162.37=162.48 (m, 2F).

Reactions of Surfaces with Diazonium Salts

The cleaned, prepared surface materials were brought inside a low-oxygen N$_2$-atmosphere glove box. Inside the glove box, a solution of the diazonium salt was made to 0.5 mM concentration in acetonitrile, providing enough volume to completely cover the entire sample inside a screw-cap Nalgene jar. To adequately cover a 2-inch wafer, at least 10 mL must be prepared. For the smaller shards of GaAs, 5 mL of solution is sufficient. The surface samples are immersed in the diazonium solution, sealed to prevent evaporation, and covered with foil to prevent light exposure. The reaction time was 2 hours, although shorter reaction times may be possible. Reaction times longer than 6 hours tended to create multilayers up to 3.5-5 nm thick, depending on the molecule that was used (layer thicknesses were determined by ellipsometry). At the end of the reaction, the samples were brought out of the glove box, rinsed with acetonitrile and soaked for 5 minutes (to remove residual diazonium salt), and then rinsed with $CH_2Cl_2$ (to remove physisorbed hydrocarbons) and soaked for 1 minute. The samples were removed from the $CH_2Cl_2$ and then dried thoroughly with N$_2$.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is:

1. A hybrid molecular electronic device, comprising:
    a silicon-on-insulator substrate comprising:
        a top silicon substrate comprising a top silicon surface;
        a bottom silicon substrate comprising a bottom silicon surface; and
        an insulating layer between the top silicon substrate and the bottom silicon substrate;
    a first doped region and a second doped region;
        wherein the first doped region and the second doped region are formed within the top silicon substrate;
        wherein the first doped region and the second doped region are spaced apart so as to form a channel region between the first doped region and the second doped region; and
        wherein the first doped region comprises a source and the second doped region comprises a drain;
    a molecular layer grafted on to the channel region;
        wherein the molecular layer comprises molecules comprising at least one aryl group bound to the channel region by an aryl carbon-silicon covalent bond; and
    a metallization layer comprising a gate electrode deposed on the molecular layer;
        wherein the molecules modify a conductivity of the hybrid molecular electronic device in the presence of a gate voltage applied through the metallization layer.

2. The hybrid molecular electronic device of claim 1, wherein the molecular layer comprises a molecular monolayer.

3. A hybrid molecular electronic device, comprising:
    a silicon-on-insulator substrate, comprising:
        a bottom silicon substrate;
        a top silicon substrate; and
        an insulating layer between the top silicon substrate and the bottom silicon substrate;
    a metallization layer comprising a gate electrode formed on a bottom surface of the bottom silicon substrate;
    a first doped region and a second doped region;
        wherein the first doped region and the second doped region are formed within the top silicon substrate;
        wherein the first doped region and the second doped region are spaced apart so as to form a channel region between the first doped region and the second doped region; and
        wherein the first doped region comprises a source and the second doped region comprises a drain; and
    a molecular layer grafted on to the channel region;
        wherein the molecular layer comprises molecules comprising at least one aryl group bound to the channel region by an aryl carbon-silicon covalent bond; and wherein the molecules modify a conductivity of the hybrid molecular electronic device in the presence of a gate voltage applied through the metallization layer.

4. The hybrid molecular electronic device of claim 3, wherein the hybrid molecular electronic device comprises a molecular field effect transistor selected from the group consisting of an n-channel transistor and a p-channel transistor.

5. The hybrid molecular electronic device of claim 3, wherein the hybrid molecular electronic device comprises a device selected from the group consisting of an enhancement mode transistor, a depletion mode transistor, a memory element, and a chemical sensor.

6. The hybrid molecular electronic device of claim 3, wherein the molecular layer comprises a molecular monolayer.

7. The hybrid molecular electronic device of claim 3, wherein the top silicon substrate comprises p-type silicon; and
wherein the first doped region comprises an n+ region and the second doped region comprises an n+ region.

8. The hybrid molecular electronic device of claim 3, further comprising:
a third doped region in the channel region.

9. The hybrid molecular electronic device of claim 8, wherein a doping in the third doped region is limited to a top surface of the top silicon substrate.

10. The hybrid molecular electronic device of claim 8, wherein the third doped region comprises an n− region.

11. The hybrid molecular electronic device of claim 3, wherein the molecules comprising the molecular layer are selectively reactive with target molecules; and
wherein a reaction between the molecules comprising the molecular layer and the target molecules causes a change in the conductivity across the channel region between the first doped region and the second doped region.

12. The hybrid molecular electronic device of claim 3, further comprising:
a first metallic contact and a second metallic contact;
wherein the first metallic contact is disposed on the first doped region; and
wherein the second metallic contact is disposed on the second doped region.

13. A hybrid molecular electronic device, comprising:
a substrate layer comprising a top surface and a bottom surface;
a gate electrode connected to the bottom surface of the substrate layer;
a first doped region and a second doped region, each contacting the top surface of the substrate layer;
wherein the first doped region and the second doped region are spaced apart so as to form a channel region between the first doped region and the second doped region; and
wherein the first doped region comprises a source and the second doped region comprises a drain; and
a molecular layer grafted on to the channel region;
wherein the molecular layer comprises molecules comprising at least one aryl group bound to the channel region by an aryl carbon-substrate covalent bond; and
wherein the molecules modify a conductivity of the hybrid molecular electronic device in the presence of a gate voltage applied through the gate electrode.

14. The hybrid molecular electronic device of claim 13, wherein the molecular layer comprises a molecular monolayer.

15. The hybrid molecular electronic device of claim 13, wherein the substrate layer comprises p-type silicon; and
wherein the first doped region and the second doped region comprise n+ regions.

16. The hybrid molecular electronic device of claim 13, further comprising:
a third doped region in the channel region.

17. The hybrid molecular electronic device of claim 16, wherein a doping in the third doped region is limited to the top surface of the substrate layer.

18. The hybrid molecular electronic device of claim 16, wherein the third doped region comprises an n− region.

19. The hybrid molecular electronic device of claim 13, wherein the conductivity is modified from a first conductivity condition to a second conductivity condition; and
wherein the first conductivity condition represents a first memory state and the second conductivity condition represents a second memory state.

20. The hybrid molecular electronic device of claim 13, further comprising:
a first metallic contact and a second metallic contact;
wherein the first metallic contact is disposed on the first doped region; and
wherein the second metallic contact is disposed on the second doped region.

21. A hybrid molecular electronic device, comprising:
a substrate layer comprising a top surface and a bottom surface;
a first doped region and a second doped region, each contacting the top surface of the substrate layer;
wherein the first doped region and the second doped region are spaced apart so as to form a channel region between the first doped region and the second doped region; and
wherein the first doped region comprises a source and the second doped region comprises a drain;
a molecular layer grafted on to the channel region;
wherein the molecular layer comprises molecules comprising at least one aryl group bound to the channel region by an aryl carbon-substrate covalent bond; and
a gate electrode deposed on the molecular layer;
wherein the molecules modify a conductivity of the hybrid molecular electronic device in the presence of a gate voltage applied through the gate electrode.

22. The hybrid molecular electronic device of claim 21, wherein the molecular layer comprises a molecular monolayer.

* * * * *